(12) United States Patent
Tsunomori et al.

(10) Patent No.: US 10,242,445 B2
(45) Date of Patent: *Mar. 26, 2019

(54) DYNAMIC ANALYSIS APPARATUS AND DYNAMIC ANALYSIS SYSTEM

(71) Applicant: Konica Minolta, Inc., Chiyoda-ku, Tokyo (JP)

(72) Inventors: Akinori Tsunomori, Kodaira (JP); Koichi Fujiwara, Osaka (JP); Sho Noji, Kokubunji (JP); Hitoshi Futamura, Hachioji (JP); Satoshi Kasai, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/913,982

(22) Filed: Mar. 7, 2018

(65) Prior Publication Data

US 2018/0197289 A1 Jul. 12, 2018

Related U.S. Application Data

(63) Continuation of application No. 15/145,137, filed on May 3, 2016, now Pat. No. 9,947,093.

(51) Int. Cl.
*G06T 7/00* (2017.01)
*G06T 7/13* (2017.01)
(Continued)

(52) U.S. Cl.
CPC ............ *G06T 7/0012* (2013.01); *A61B 5/026* (2013.01); *A61B 5/7267* (2013.01); *A61B 6/507* (2013.01);
(Continued)

(58) Field of Classification Search
CPC . G06T 7/0012; G06T 7/11; G06T 7/20; G06T 7/254; G06T 7/97;
(Continued)

(56) References Cited

U.S. PATENT DOCUMENTS 9,947,093 B2 * 4/2018 Tsunomori et al. .. G06T 7/0012
2009/0097731 A1 4/2009 Sanada et al.
2015/0245776 A1 9/2015 Hirohata et al.

FOREIGN PATENT DOCUMENTS

JP 2014128687 A 7/2014

OTHER PUBLICATIONS

USPTO Notice of Allowance corresponding to U.S. Appl. No. 15/145,137; dated Dec. 8, 2017.

\* cited by examiner

*Primary Examiner* — Andrew W Johns
(74) *Attorney, Agent, or Firm* — Cantor Colburn LLP (57) ABSTRACT

A dynamic analysis apparatus may include a setting section which sets a target region in a lung region of a chest dynamic image; a conversion section which calculates a representative value of a pixel signal value in the target region, and converts the pixel signal value; an extraction section which extracts a pulmonary blood flow signal from the image; and a calculation section which calculates a change in the pulmonary blood flow signal, and calculates a feature amount regarding pulmonary blood flow. The setting section may determine a size of the target region based on a size of a body part other than a lung blood vessel, a movement amount of a body part other than the lung blood vessel or subject information of the chest dynamic image, the subject information regarding a subject of the radiation imaging, and the setting section may set the target region.

8 Claims, 9 Drawing Sheets

(51) Int. Cl.
*A61B 5/00* (2006.01)
*A61B 6/00* (2006.01)
*G06K 9/46* (2006.01)
*G06K 9/62* (2006.01)
*G06T 7/20* (2017.01)
*A61B 5/026* (2006.01)
*G06K 9/00* (2006.01)

(52) U.S. Cl.
CPC .......... *A61B 6/5217* (2013.01); *G06K 9/0053* (2013.01); *G06K 9/46* (2013.01); *G06K 9/4642* (2013.01); *G06K 9/62* (2013.01); *G06K 9/627* (2013.01); *G06T 7/0085* (2013.01); *G06T 7/13* (2017.01); *G06T 7/20* (2013.01); *A61B 6/463* (2013.01); *A61B 6/5235* (2013.01); *G06K 2209/051* (2013.01); *G06T 2207/10116* (2013.01); *G06T 2207/20008* (2013.01); *G06T 2207/30061* (2013.01); *G06T 2207/30104* (2013.01)

(58) Field of Classification Search
CPC . G06T 2207/20061; G06T 2207/30104; A61B 5/02; A61B 5/026; A61B 5/08; A61B 5/7264; A61B 5/7267; A61B 6/504; A61B 6/507; A61B 6/5217; A61B 6/5294
See application file for complete search history.

| SEX | TARGET REGION SIZE |
|---|---|
| MALE | 5 × 5mm |
| FEMALE | 3 × 3mm |

FIG.4B

| AGE | TARGET REGION SIZE |
|---|---|
| 10s | 7 × 7mm |
| 20s | 7 × 7mm |
| 30s | 5 × 5mm |
| 40s | 5 × 5mm |
| 50s | 5 × 5mm |
| 60s | 3 × 3mm |
| 70s | 3 × 3mm |

MIDLINE

DYNAMIC ANALYSIS APPARATUS AND DYNAMIC ANALYSIS SYSTEM

CROSS REFERENCE TO RELATED APPLICATION

The present application is a continuation application of U.S. patent application Ser. No. 15/145,137, filed on May 3, 2016, the entire contents of which are incorporated herein by reference and priority to which is hereby claimed.

BACKGROUND OF THE INVENTION

Field of the Invention

The present invention relates to a dynamic analysis apparatus and a dynamic analysis system.

Description of Related Art

Attempts have been made to use semiconductor image sensors such as FPDs (flat panel detectors) for capturing dynamic images at diagnosis target sites and use the dynamic images for diagnosis instead of capturing and diagnosing still images of radiation (X-ray) using conventional films/screens and stimulable phosphor plates. Specifically, by using rapid responsiveness of a semiconductor image sensor in reading and deleting image data, pulsed radiation is continuously emitted from a radiation source at the reading and deleting timings of the semiconductor image sensor, and imaging is performed a plurality of times per second to capture images of a dynamic state at a diagnosis target site. By sequentially displaying a series of images captured by the imaging, a doctor can observe a series of movements at the diagnosis target site.

In diagnosis of a lung, it is important to observe the lung to find a point where a lung function (ventilation function and pulmonary blood flow function) is lowered. However, there is difficulty in observing the dynamic state image and visually recognizing the functionally abnormal point for a doctor. Especially, the lung's respiratory motion and the heart beat are different between individuals, and thus, it is difficult to visually confirm the abnormal point of ventilation function and pulmonary blood flow function in consideration of the difference between individuals.

Thus, it has been suggested to analyze a series of frame images obtained by dynamic imaging, generate diagnosis support information and provide the diagnosis support information to a doctor for early diagnosis.

For example, Patent document 1 (Japanese Patent Application Laid Open Publication No. 2014-128687) describes a system in which a lung region in a dynamic image, which was captured while the subject was breathing, is divided into a plurality of small regions, information regarding the amount of pulmonary blood flow is generated by calculating an average value of pixel values and applying a high pass filter in a time direction for each of the small regions, and phase delay time of a temporal change of information regarding pulmonary blood flow with respect to a temporal change of a signal indicating the heart beat is calculated and displayed. The size of each small region is described to be 0.4 to 4 cm square.

The movements of body parts in the lung are very large compared to the change of pulmonary blood flow. Thus, in order to analyze the dynamic image and obtain information regarding the change of pulmonary blood flow function, it is preferable that the imaging is performed while the subject holds the breath to suppress the movements of the body parts due to breathing. However, in some cases, the breath-holding is impossible due to diseases and such like, and an analysis method using a dynamic image captured without holding the breath is desired.

The Patent document 1 analyzes a chest dynamic image captured under a breathing state, and suppresses the noises other than a blood flow signal component by averaging the pixel values in the small regions and applying a high pass filter. However, the size of small region is not appropriate for removing the influences such as the movements of body parts and differences between individuals. Thus, the movements of body parts, differences between individuals and such like appear as a noise in some cases.

SUMMARY OF THE INVENTION

An object of the present invention is to set a size of a target region for suppressing a noise to be an appropriate size when a pulmonary blood flow function is analyzed in a chest dynamic image.

In order to solve the above problems, according to one aspect of the present invention, there is provided a dynamic analysis apparatus, including: a setting section which sets a plurality of target regions in a lung region of a chest dynamic image which is obtained by radiation imaging; a conversion section which calculates a representative value of a pixel signal value in the target region set by the setting section, and converts the pixel signal value in the target region on the basis of the calculated representative value; an extraction section which extracts a pulmonary blood flow signal from the chest dynamic image after conversion by the conversion section; and a calculation section which calculates a change amount of the pulmonary blood flow signal extracted by the extraction section, and calculates a feature amount regarding pulmonary blood flow on the basis of the calculated change amount of the pulmonary blood flow signal, wherein the setting section determines a size of the target region on the basis of a size of a body part other than a lung blood vessel in the chest dynamic image, a movement amount of a body part other than the lung blood vessel or subject information attached to the chest dynamic image, the subject information being information regarding a subject of the radiation imaging, and the setting section sets the target region having the determined size in the lung region of the chest dynamic image.

According to another aspect of the present invention, there is provided a dynamic analysis system, including: an imaging apparatus which obtains a chest dynamic image by performing radiation imaging of a dynamic state at a chest of a human body; and the dynamic analysis apparatus according to claim 1.

BRIEF DESCRIPTION OF THE DRAWINGS

The above and other objects, advantages and features of the present invention will become more fully understood from the detailed description given hereinafter and the appended drawings which are given by way of illustration only, and thus are not intended as a definition of the limits of the present invention, and wherein.

DETAILED DESCRIPTION OF THE PREFERRED EMBODIMENT

Hereinafter, an embodiment of the present invention will be described in detail with reference to the drawings. However, the scope of the present invention is not limited to the illustrated examples.

[Configuration of Dynamic Analysis System 100]

First, the configuration will be described.

Figure 1:
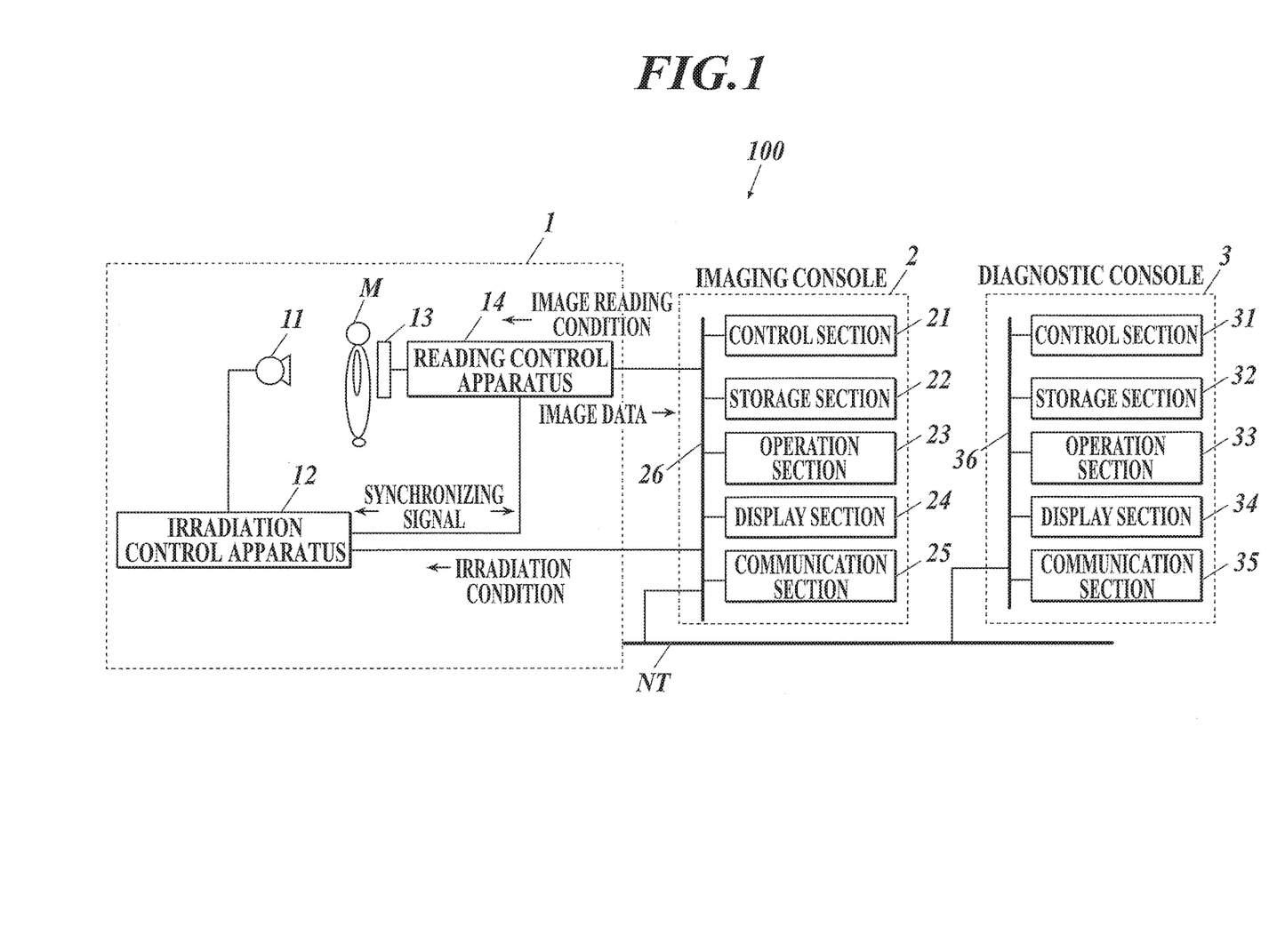
FIG. 1 is a view showing the entire configuration of a dynamic analysis system in an embodiment of the present invention.

FIG. 1 shows the entire configuration of a dynamic analysis system 100 in the embodiment.

As shown in FIG. 1, the dynamic analysis system 100 is configured by connecting an imaging apparatus 1 to an imaging console 2 by a communication cable and such like, and connecting the imaging console 2 to a diagnostic console 3 via a communication network NT such as a LAN (Local Area Network). The apparatuses forming the dynamic analysis system 100 are compliant with the DICOM (Digital Image and Communications in Medicine) standard, and the apparatuses are communicated with each other according to the DICOM.

[Configuration of Imaging Apparatus 1]

The imaging apparatus 1 performs imaging of a dynamic state having a cycle at a chest, such as the state change of inflation and deflation of a lung according to respiratory motion and the heart beat, for example. The dynamic imaging means obtaining a plurality of images showing a dynamic state by repeatedly emitting a pulsed radiation such as X-ray to a subject at a predetermined time interval (pulse irradiation) or continuously emitting the radiation (continuous irradiation) at a low dose rate without interruption. A series of images obtained by the dynamic imaging is referred to as a dynamic image. Each of the plurality of images forming the dynamic image is referred to as a frame image. Hereinafter, the embodiment will be described by taking, as an example, a case where the dynamic imaging is performed by pulse irradiation.

A radiation source 11 is located at a position facing a radiation detection section 13 through a subject M, and emits radiation (X ray) to the subject M in accordance with control of an irradiation control apparatus 12.

The irradiation control apparatus 12 is connected to the imaging console 2, and performs radiation imaging by controlling the radiation source 11 on the basis of an irradiation condition which was input from the imaging console 2. The irradiation condition input from the imaging console 2 is a pulse rate, a pulse width, a pulse interval, the number of imaging frames per imaging, a value of X-ray tube current, a value of X-ray tube voltage and a type of applied filter, for example. The pulse rate is the number of irradiation per second and consistent with an after-mentioned frame rate. The pulse width is an irradiation time required for one irradiation. The pulse interval is a time from start of one irradiation to start of next irradiation, and consistent with an after-mentioned frame interval.

The radiation detection section 13 is configured by including a semiconductor image sensor such as an FPD. The FPD has a glass substrate, for example, and a plurality of detection elements (pixels) is arranged in matrix at a predetermined position on the substrate to detect, according to the intensity, at least radiation which was emitted from the radiation source 11 and has transmitted through the subject M, and convert the detected radiation into electric signals to be accumulated. Each pixel is formed of a switching section such as a TFT (Thin Film Transistor), for example. The FPD may be an indirect conversion type which converts X ray into an electrical signal by photoelectric conversion element via a scintillator, or may be a direct conversion type which directly converts X ray into an electrical signal.

The radiation detection section 13 is provided to face the radiation source 11 via the subject M.

The reading control apparatus 14 is connected to the imaging console 2. The reading control apparatus 14 controls the switching sections of respective pixels in the radiation detection section 13 on the basis of an image reading condition input from the imaging console 2, switches the reading of electric signals accumulated in the pixels, and reads out the electric signals accumulated in the radiation detection section 13 to obtain image data. The image data is a frame image. The reading control apparatus 14 outputs the obtained frame image to the imaging console 2. The image reading condition includes a frame rate, frame interval, a pixel size, an image size (matrix size) and such like. The frame rate is the number of frame images obtained per second and consistent with the pulse rate. The frame interval is a time from start of obtaining one frame image to start of obtaining the next frame image, and consistent with the pulse interval.

Here, the irradiation control apparatus 12 and the reading control apparatus 14 are connected to each other, and transmit synchronizing signals to each other to synchronize the irradiation operation with the image reading operation.

[Configuration of Imaging Console 2]

The imaging console 2 outputs the irradiation condition and the image reading condition to the imaging apparatus 1, controls the radiation imaging and reading operation of radiation images by the imaging apparatus 1, and displays the dynamic image obtained by the imaging apparatus 1 for an operator who performs the imaging such as an imaging operator to confirm positioning and whether the image is appropriate for diagnosis.

As shown in FIG. 1, the imaging console 2 is configured by including a control section 21, a storage section 22, an operation section 23, a display section 24 and a communication section 25, which are connected to each other via a bus 26.

The control section 21 is configured by including a CPU (Central Processing Unit), a RAM (Random Access Memory) and such like. According to the operation of operation section 23, the CPU of the control section 21 reads out system programs and various processing programs stored in the storage section 22 to load the programs into the RAM, executes various types of processing including after-mentioned imaging control processing in accordance with the loaded program, and integrally controls the operations of sections in the imaging console 2 and the irradiation operation and reading operation of the imaging apparatus 1.

The storage section 22 is configured by including a non-volatile semiconductor memory and a hard disk. The storage section 22 stores various programs executed by the control section 21, parameters necessary for executing processing by the programs, and data of processing results. For example, the storage section 22 stores a program for executing the imaging control processing shown in FIG. 2. The storage section 22 stores the irradiation condition and the image reading condition corresponding to the imaging site (here, chest). The various programs are stored in a form of readable program code, and the control section 21 executes the operation according to the program code as needed.

The operation section 23 is configured by including a keyboard including cursor keys, numeric keys and various function keys and a pointing device such as a mouse. The operation section 23 outputs an instruction signal input by a key operation to the keyboard or a mouse operation to the control section 21. The operation section 23 may include a touch panel on the display screen of display section 24. In this case, the operation section 23 outputs the input instruction signal to the control section 21 via the touch panel.

The display section 24 is configured by a monitor such as an LCD (Liquid Crystal Display) and a CRT (Cathode Ray Tube), and displays instructions input from the operation section 23, data and such like in accordance with an instruction of a display signal input from the control section 21.

The communication section 25 includes a LAN adapter, a modem, a TA (Terminal Adapter) and such like, and controls the data transmission and reception with the apparatuses connected to the communication network NT.

[Configuration of Diagnostic Console 3]

The diagnostic console 3 is a dynamic analysis apparatus for obtaining the dynamic image from the imaging console 2 and displaying the obtained dynamic image and analysis result of the dynamic image to support diagnosis by a doctor. In the embodiment, the diagnostic console 3 analyses a dynamic image of chest for a pulmonary blood flow function, and displays the analysis result.

As shown in FIG. 1, the diagnostic console 3 is configured by including a control section 31, a storage section 32, an operation section 33, a display section 34 and a communication section 35, which are connected to each other via a bus 36.

The control section 31 is configured by including a CPU, a RAM and such like. According to the operation of the operation section 33, the CPU of the control section 31 reads out system programs stored in the storage section 32 and various processing programs to load them into the RAM, executes the various types of processing including after-mentioned image analysis processing in accordance with the loaded program, and integrally controls operations of the sections in the diagnostic console 3. The control section 31 functions as a setting section, a conversion section, an extraction section, a calculation section and a comparison section.

The storage section 32 is configured by including a non-volatile semiconductor memory, a hard disk and such like. The storage section 32 stores various programs including a program for executing the image analysis processing by the control section 31, parameters necessary for executing processing by the programs and data of processing results. The various programs are stored in a form of readable program code, and the control section 31 executes the operation according to the program code as needed.

The operation section 33 is configured by including a keyboard including cursor keys, numeric keys and various function keys and a pointing device such as a mouse, and outputs an instruction signal input by a key operation to the keyboard and a mouse operation to the control section 31. The operation section 33 may include a touch panel on the display screen of the display section 34. In this case, the operation section 33 outputs an instruction signal, which was input via the touch panel, to the control section 31.

The display section 34 is configured by including a monitor such as an LCD and a CRT, and performs various displays in accordance with the instruction of display signal input from the control section 31.

The communication section 35 includes a LAN adapter, a modem, a TA and such like, and controls data transmission and reception with the apparatuses connected to the communication network NT.

[Operation of Dynamic Analysis System 100]

Next, the operation of the dynamic analysis system 100 will be described.

(Operations of Imaging Apparatus 1 and Imaging Console 2)

First, imaging operation by the imaging apparatus 1 and the imaging console 2 will be described.

Figure 2:
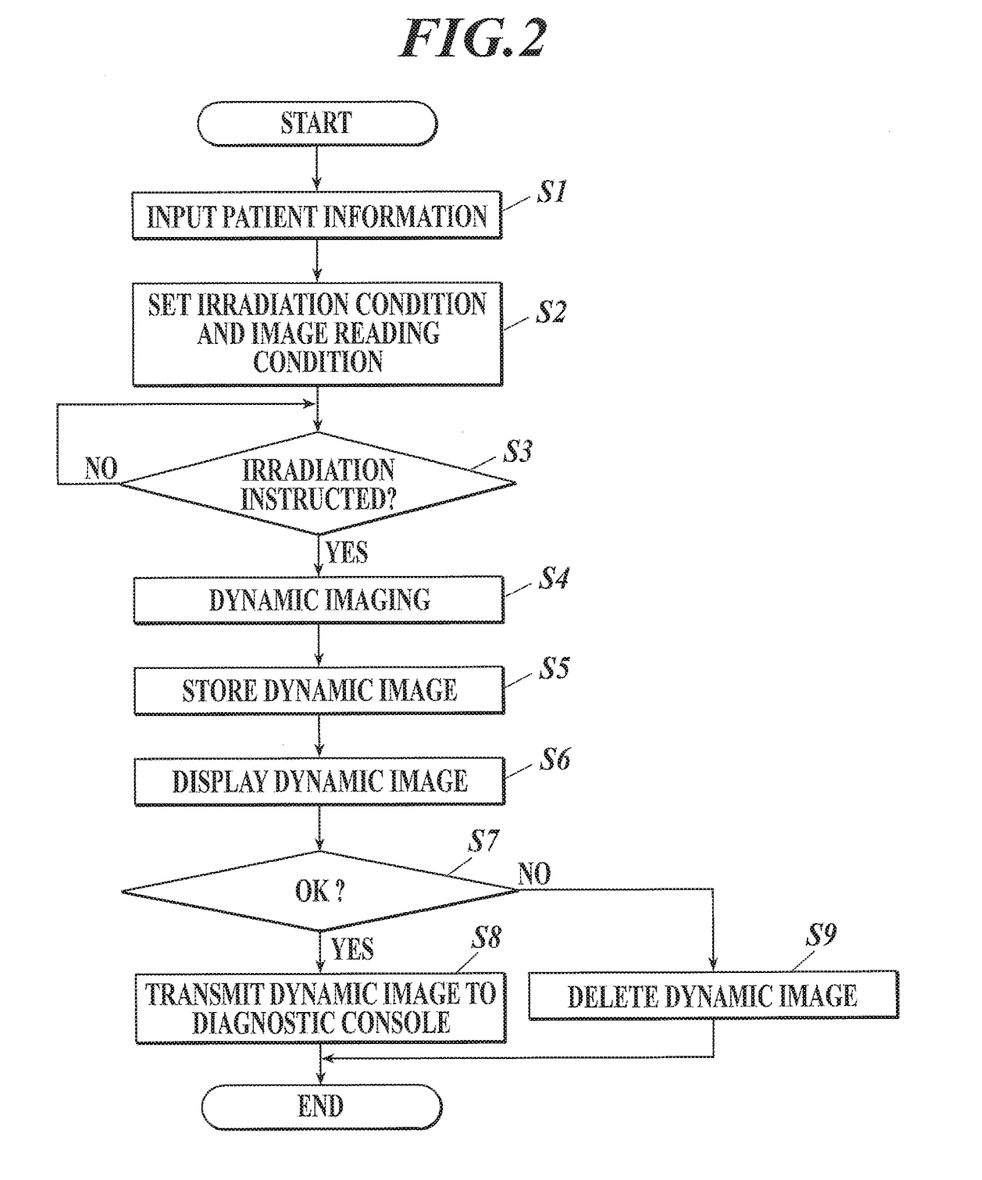
FIG. 2 is a flowchart showing imaging control processing executed by a control section of an imaging console in FIG. 1.

FIG. 2 shows imaging control processing executed by the control section 21 in the imaging console 2. The imaging control processing is executed in cooperation between the control section 21 and the program stored in the storage section 22.

First, the operator operates the operation section 23 in the imaging console 2, and inputs patient information (patient name, height, weight, age, sex and such like) of the imaging target (subject M) and imaging site (here, chest) (step S1).

Next, the irradiation condition is read out from the storage section 22 and set in the irradiation control apparatus 12, and the image reading condition is read out from the storage section 22 and set in the reading control apparatus 14 (step S2).

An instruction of irradiation by the operation of operation section 23 is waited (step S3). The operator locates the subject M between the radiation source 11 and the radiation detection section 13, and performs positioning. Since the imaging is performed while the subject M is breathing in the embodiment, the operator instructs the subject of imaging (subject M) to be at ease to lead the subject M into quiet breathing. When the preparation for imaging is completed, the operator operates the operation section 23 to input an irradiation instruction.

When the irradiation instruction is input from the operation section 23 (step S3: YES), the imaging start instruction is output to the irradiation control apparatus 12 and the reading control apparatus 14, and the dynamic imaging is started (step S4). That is, radiation is emitted by the radiation source 11 at the pulse interval set in the irradiation control apparatus 12, and frame images are obtained by the radiation detection section 13.

When the imaging is finished for a predetermined number of frames, the control section 21 outputs an instruction to end the imaging to the irradiation control apparatus 12 and the reading control apparatus 14, and the imaging operation is stopped. The imaging is performed to obtain the number of frame images which can image at least one respiratory cycle.

The frame images obtained by the imaging are input to the imaging console 2 in order, stored in the storage section 22 so as to be associated with respective numbers (frame numbers) indicating the imaging order (step S5), and displayed on the display section 24 (step S6). The operator confirms positioning and such like by the displayed dynamic image, and determines whether an image appropriate for diagnosis was acquired by the imaging (imaging was successful) or imaging needs to be performed again (imaging failed). The operator operates the operation section 23 and inputs the determination result.

If the determination result indicating that the imaging was successful is input by a predetermined operation of the operation section 23 (step S7: YES), each of a series of frame images obtained by the dynamic imaging is accompanied with information such as identification ID for identifying the dynamic image, patient information, imaging site, irradiation condition, image reading condition and number (frame number) indicating the imaging order (for example, the information is written into a header region of image data in the DICOM format), and transmitted to the diagnostic console 3 via the communication section 25 (step S8). Then, the processing ends. On the other hand, if the determination result indicating that the image failed is input by a predetermined operation of operation section 23 (step S7: NO), the series of frame images stored in the storage section 22 is deleted (step S9), and the processing ends. In this case, the imaging needs to be performed again.

(Operation of Diagnostic Console 3)

Next, the operation of diagnostic console 3 will be described.

Figure 3:
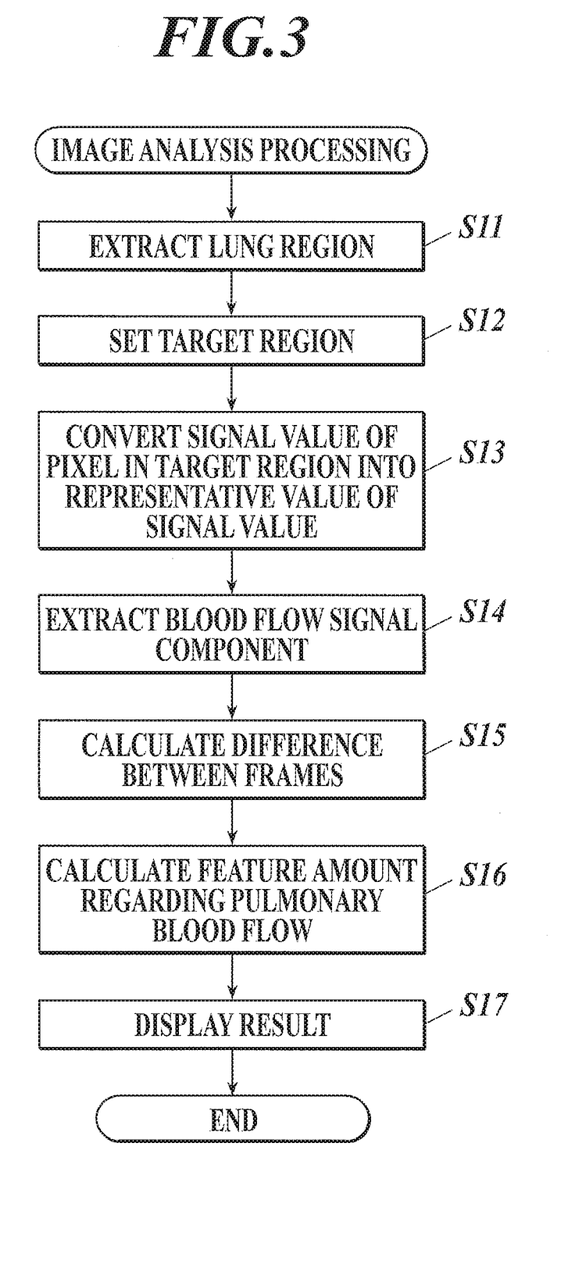
FIG. 3 is a flowchart showing image analysis processing executed by a control section of a diagnostic console in FIG. 1.

In the diagnostic console 3, when a series of frame images forming a dynamic image is received from the imaging console 2 via the communication section 35, the image analysis processing shown in FIG. 3 is executed in cooperation between the control section 31 and the program stored in the storage section 32.

Hereinafter, the flow of image analysis processing will be described with reference to FIG. 3.

First, a lung region which is the analysis target region is extracted from each of the frame images forming the dynamic image (step S11).

Any method may be used as the method for extracting the lung region. For example, a threshold value is obtained by a discriminant analysis from histogram of signal value (density value) for each pixel of the frame image, and the region having higher signals than the threshold value is primarily extracted as a lung region candidate. Then, edge detection is performed around the border of the lung region candidate which was primarily extracted, and the points having largest edges in small blocks around the border are extracted along the border to extract the border of lung region.

A target region which is a unit of noise removal is set in the lung region of each frame image forming the dynamic image (step S12).

In step S12, the size of target region is determined first. The target region size is determined on the basis of, for example, one of i) size of lung, ii) patient information (sex, age, height and such like of patient), iii) movement amount of diaphragm and iv) movement amount of rib. Hereinafter, the method for determining the target region size based on each of the above items will be described.

i) Determination of Target Region Size Based on the Size of Lung

As a condition for determining the target region size by this determination method, mean areas of lung (mean area of right lung: Mean (Sright) and mean area of left lung: Mean (Sleft)) among a plurality of different human bodies and a standard target region size (Broi_x, Broi_y) are stored in the program in advance. The standard target region size is the most appropriate target region size for the lung having an average area, and obtained experimentally and empirically.

First, the mean areas (mean area of right lung: Sright, mean area of left lung: Sleft) are calculated for the lungs in the series of frame images forming the dynamic image. For example, an area is calculated by counting the number of pixels in a region and multiplying the counted number by the pixel size for each of the right lung region and left lung region in each of the frame images, and the mean value of the calculated areas of the respective frame images is calculated.

Next, on the basis of the calculated mean area, (Roix, Roiy) is calculated by the following (Expression 1) and (Expression 2), and the calculated size is determined as the target region size (width×length). Though the (Expression 1) and (Expression 2) are expressions for the right lung, the target region size of left lung can also be calculated similarly.

$$Roix = Broi\_x \times (Sright/Mean(Sright)) \quad \text{(Expression 1)}$$

$$Roiy = Broi\_y \times (Sright/Mean(Sright) \quad \text{(Expression 2)}$$

By determining the target region size on the basis of the area of lung, the target region size can be set to be the most appropriate size according to the lung size. As a result, for example, it is possible to prevent a large target region appropriate for an adult from being set to a small lung of a child.

ii) Determination of Target Region Size Based on Patient Information (Sex, Age and Height of Patient)

Figure 4A:
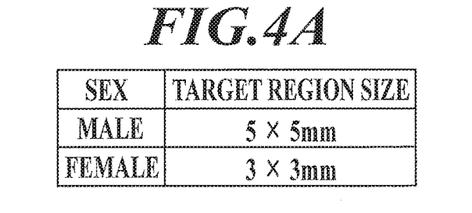
FIG. 4A is a view showing an example of a conversion table between a sex and a target region size.
Figure 4B:
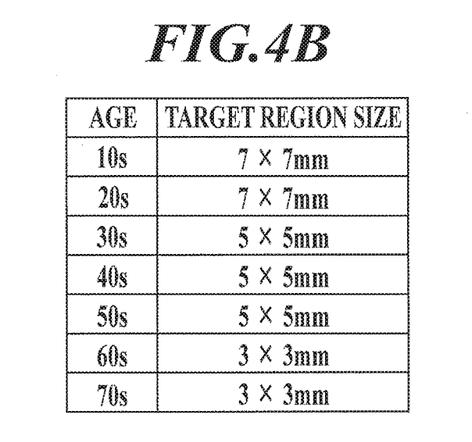
FIG. 4B is a view showing an example of a conversion table between an age and a target region size.

Since males perform abdominal breathing dominantly, males move their lungs more largely than females. In addition, the lung moves worse with aging. Thus, a conversion table (see FIGS. 4A and 4B) associating the target region size with each of the sex and age is stored in the storage section 32, the conversion table is referred to, and the target region size is determined on the basis of sex and age of the patient information (subject of the imaging) included in the accompanying information attached to the dynamic image. Though FIGS. 4A and 4B respectively show the conversion tables of sex and age, an age-based conversion table for a male and an age-based conversion table for a female may be stored in the storage section 32. The base for determination is not limited to sex and age, and a conversion table associating the target region size with other physical information such as height and weight may be stored in the storage section 32.

iii) Determination of Target Region Size Based on Movement Amount of Diaphragm

Figure 5:
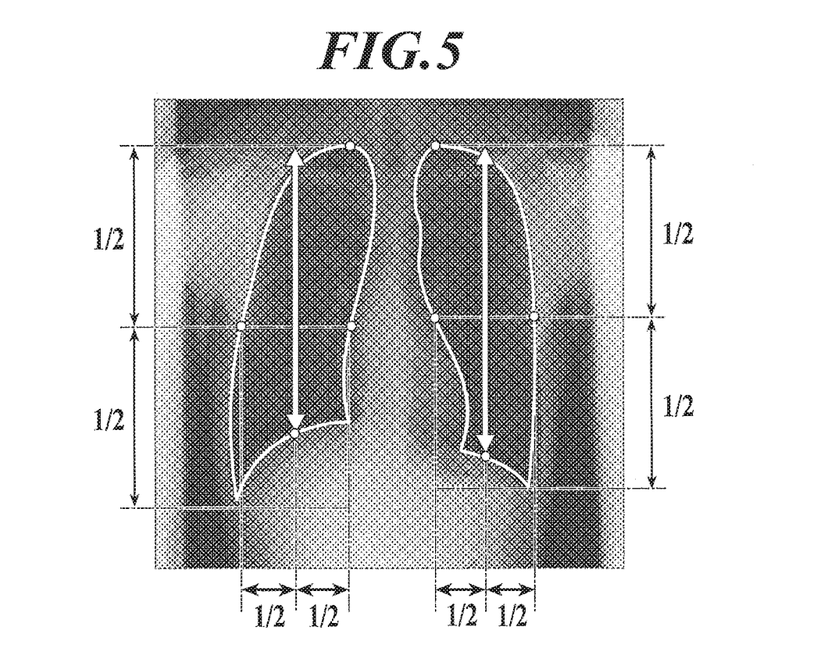
FIG. 5 is a view for explaining a determination method of a measurement point when a movement amount of diaphragm is measured.

The movement amount of diaphragm can be obtained by a method described in a known document 1, for example (known document 1: Development of low-cost and low-dose portable functional X-ray imaging"Visual stethoscope", Rie TANAKA, Shigeru SANADA, Medical Imaging and Information Sciences Vol. 31 (2014) No. 2). In the first frame, the four measurement points shown in FIG. 5 (an apex in the lung apex and a point in the diaphragm dome for each of left and right lungs) are determined by edge detection. In the second frame and the following frames, the measurement points are traced by template matching. The change amount of the apex-diaphragm distance (distance between the lung apex and the diaphragm) is the diaphragm movement amount. For example, the calculated maximum diaphragm movement amount (difference between the largest value and the smallest value of the apex-diaphragm distances) is determined as a target region size (length of a side of the target region).

iv) Determination of Target Region Size Based on Movement Amount of Rib

Figure 6A:
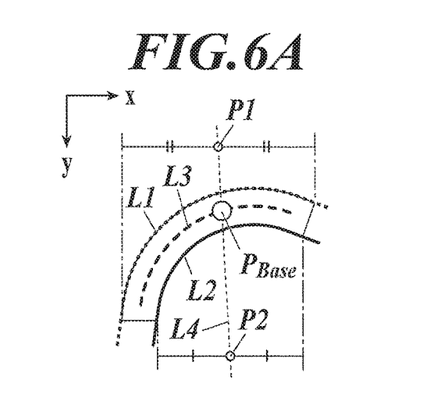
FIG. 6A is a view for explaining a determination method of a representative point when a movement amount of a rib is measured.
Figure 6B:
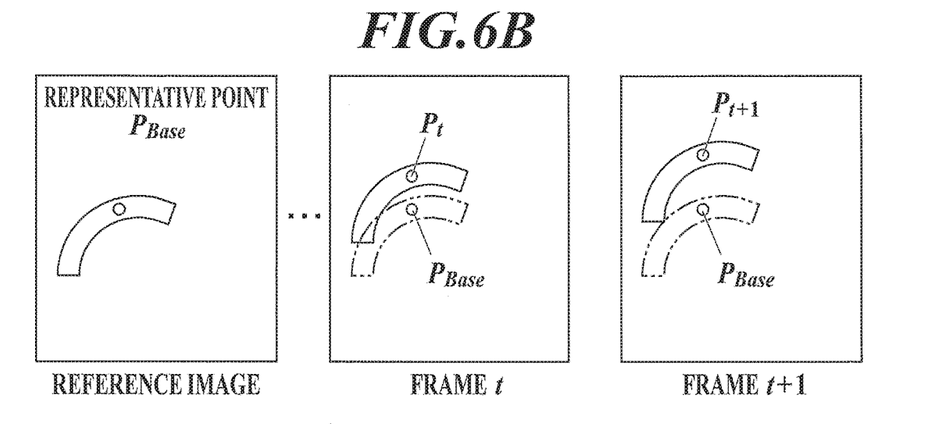
FIG. 6B is a view for explaining the determination method of representative point when the movement amount of the rib is measured.

First, the upper edge and lower edge of a rib are extracted from the lung region in each of the frame images. The upper and lower edges of a rib can be extracted by a known image processing technique such as a rib extraction method using the model function and Sobel operator described in Japanese Patent Application Laid Open Publication No. H5-176919, for example. Then, the movement amount of the rib is calculated. For example, as shown in FIG. 6A, in a reference image (such as an image of resting expiratory level), an intermediate curve L3 between the extracted upper edge L1 and lower edge L2 of the rib is obtained, and a representative point PBase is set at the intersection of the intermediate curve L3 and a line L4 which is connecting the midpoint P1 in the x direction of the upper edge L1 and the midpoint P2 in the x direction of lower edge L3 of the rib. Similarly, representative points (Pt, Pt+1, . . . ) of the same rib are set in respective other frame images (see FIG. 6B). The distance between the representative point in the reference image and a representative point in each of the other frame images is obtained as a movement amount of the rib, and the largest value among the obtained distances is determined as a target region size (length of a side of target region), for example. The target region size may be determined by considering the width of the rib in addition to the above process.

That is, the target region size is determined according to the size or movement amount of lung region, movement amount of a body part which is a noise for analysis, or difference between individuals such as sex and age of the subject.

When the target region size is determined, an image among a series of frame images forming the dynamic image is set as a reference image, and a target region which has the determined size and is formed of a plurality of pixels is set in the lung region of the reference image. A preferable reference image is a frame image of a resting expiratory level at which the lung region has the minimum area. By the preferable reference image, when small regions in the reference image are associated with those in each of the other frame images, the small regions are not associated with regions outside the lung region in each of the other frame images.

Figure 7:
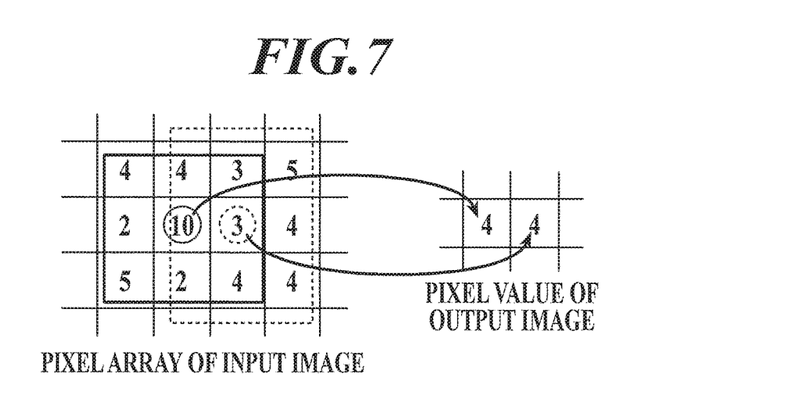
FIG. 7 is a view showing a conversion example of signal values in a case where set target regions overlap each other.

For example, the lung region in the reference image is divided into a plurality of small regions (rectangular regions) having the determined size, and each of the small regions is set as a target region. Alternatively, the reference image may be displayed on the display section 34 so that the user specifies a point on the displayed reference image by operating the operation section 33, and a rectangular region which has the determined size and includes the specified point on the upper left side is set to be a target region. In such cases, the target region is set in a tiled manner without overlapping each other. The target regions which are not overlapping in such way are referred to as non-overlapping target regions. On the other hand, the target region having the determined size may be set by being shifted by one pixel on the lung region. In this case, neighboring target regions are overlapping each other as shown in FIG. 7. The target regions overlapping each other in this way are referred to as overlapping target regions.

Next, in each of the other frame images, the target regions are set at the same pixel positions as the target regions which were set in the reference image (regions of the signal values output from the same detection elements of radiation detection section 13 used for the imaging). In the above cases of (i) and (ii), it is preferable that the target regions are set in the other frame images after correcting the positioning gaps of lung region between the frame images by performing known local matching processing and warping processing (see Japanese Patent Application Laid Open Publication No. 2012-5729).

The signal value (pixel signal value) of each pixel in each of the frame images is replaced with a representative value calculated from the pixel signal values in the target region (step S13). This process suppresses the signal components of other body parts such as ribs which are noises.

In step S13, for example, if the set target regions are non-overlapping target regions, the representative value of pixel signal values in the target region is calculated, and the signal value of each pixel in the target region is converted into the calculated representative value. If the set target regions are overlapping target regions, as shown in FIG. 7, the representative value of pixel signal values in the target region is calculated, and the signal value of the pixel located at the center of the target region is converted into the calculated representative value.

The representative value may be any one of median value, mean value, maximum value, minimum value and such like. However, the median value is preferable since the signal components of other body parts such as ribs which are noises can be suppressed more effectively.

The blood flow signal component (that is, pulmonary blood flow signal component) is extracted from the lung region of the converted dynamic image, and a plurality of frame images formed of the blood flow signal components is generated (step S14).

As the method for extracting the blood flow signal component, there are i) method using a frequency filter, ii) method using an average waveform, iii) method using machine learning and such like. Hereinafter, each of the extraction methods will be described.

i) Method Using a Frequency Filter

In a case where non-overlapping target regions are set, corresponding target regions in a series of respective frame images are associated with each other, the temporal change of signal value (representative value) is calculated for the target region, and the calculated temporal change is filtered by a high pass filter (for example, cutoff frequency is 0.7 Hz) in the time direction. This process removes the influence of ventilation by removing only the blood flow signal component from the temporal change of signal value for each target region.

In a case where overlapping target regions are set, the temporal change of signal value (representative value) is calculated for each pixel between the frames, and the calculated temporal change is filtered by a high pass filter (for example, cutoff frequency is 0.7 Hz) in the time direction. This process removes the influence of ventilation by removing only the blood flow signal component from the temporal change of signal value for each pixel.

A bandpass filter may be used instead of the high pass filter.

ii) Method Using an Average Waveform

Figures 8A, 8B:
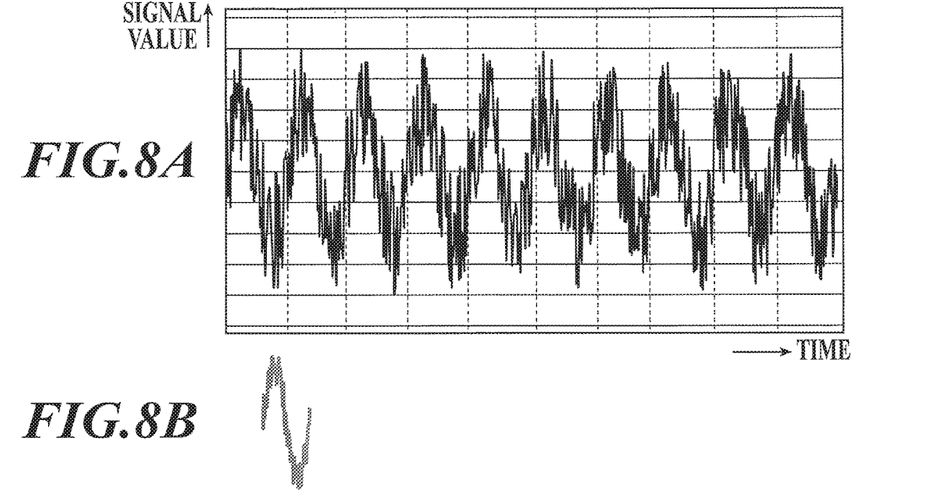
FIG. 8A is a view showing an example of original signal waveform.
FIG. 8B is a view showing an example of average signal waveform.
Figure 8C:
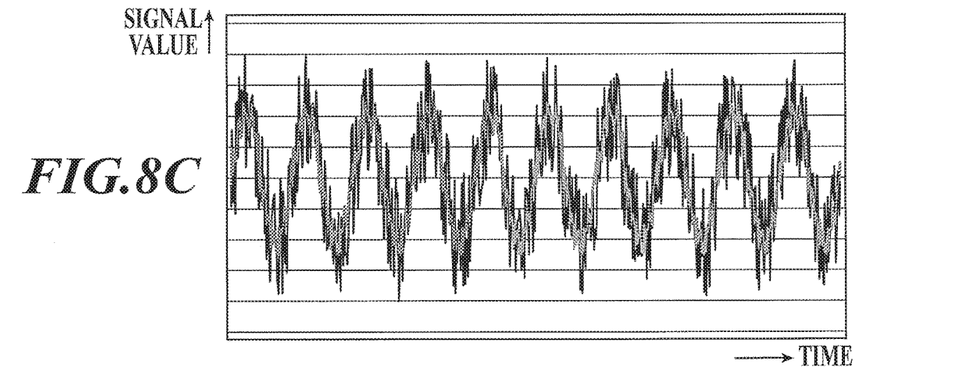
FIG. 8C is a view showing a state in which the original signal waveform in FIG. 8A and the average signal waveform in FIG. 8B are superposed.
Figure 8D:
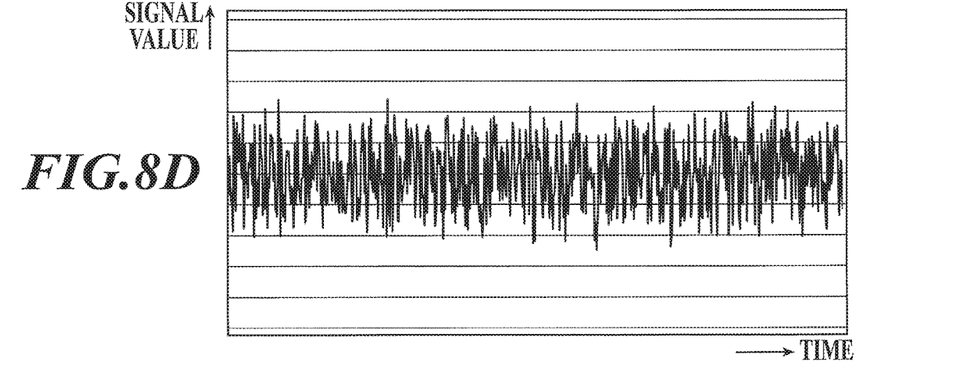
FIG. 8D is a view showing a blood flow signal component which is extracted by subtracting the average signal in FIG. 8B from the original signal component in FIG. 8A.

In a case where non-overlapping target regions are set, corresponding target regions in a series of respective frame images are associated with each other, and a waveform showing a temporal change of signal value is drawn for the target region. The signal waveform is referred to as an original signal waveform. FIG. 8A shows an example of the original signal waveform. As shown in FIG. 8A, the original signal waveform has a waveform in which a high frequency by pulmonary blood flow is superposed on a low frequency by breathing. The original signal waveform is divided by the cycle of the low frequency, and the waveforms for a plurality of cycles are averaged to generate an average signal waveform. FIG. 8B shows an example of the average signal waveform. The average signal waveform has a waveform which is nearly a sinusoidal waveform of low frequency as shown in FIG. 8B since the high frequency component is averaged. As shown in FIG. 8C, the original signal waveform and the average signal waveform are superposed on each other, the average signal is subtracted from the original signal (difference is obtained), and thereby, the high frequency component is obtained as shown in FIG. 8D. That is, the blood flow signal component can be extracted.

In a case where overlapping target regions are set, a waveform showing a temporal change of signal value (representative value) is drawn for each corresponding pixels in the respective frame images, and similarly, an average signal waveform is generated by averaging the waveforms for respective cycles of the original signal waveform. The average signal is subtracted from the original signal to extract the blood flow signal component.

iii) Method Using Machine Learning

A plurality of dynamic images imaging the dynamic state at a chest of a human body is prepared, and each of the images is filtered by a low pass filter (for example, cutoff frequency is 0.5 Hz) in the time direction to extract the signal of ventilation component. The extracted signal of ventilation component is subjected to signal reconstruction (see known document 2) by pre-training in deep learning such as RPB (Restricted Boltzmann Machine) and Auto Encoder, and a signal having a general feature of the ventilation component is generated (known document 2: A Study on Usage of Reconstruction Error of Deep Learning for Anomaly Detection on Time-Series Data, Koki Kawasaki, Tomohiro Yoshikawa, Takeshi Furuhashi, The 29th annual conference of the Japanese society for Artificial Intelligence, 2015). In a case where non-overlapping target regions are set, corresponding target regions in a series of respective frame images are associated with each other, and a waveform (original signal waveform) showing a temporal change of a signal value for the target region is generated, a signal having a general feature of ventilation component is subtracted from the original signal waveform (difference is obtained), and thereby the blood flow signal component is extracted. In a case where overlapping target regions are set, an original signal waveform showing the temporal change of signal value is generated for each corresponding pixels in the frame images, a signal having a general feature of ventilation component is subtracted from the original signal waveform (difference is obtained), and thereby a blood flow signal component is extracted.

Next, by performing inter-frame difference processing of the extracted blood flow signal component, the change amount of blood flow signal component is calculated (step S15).

In a case where non-overlapping target regions are set, the difference value of signal value between adjacent frame images is calculated for each target region. In a case where overlapping target regions are set, the difference value of signal value between adjacent frame images is calculated for each pixel, that is, for the corresponding pixels in the respective frames. Here, the inter-frame difference value is obtained by subtracting a value of a previous frame image from a value of the frame image temporally following the previous frame image.

Next, a feature amount of pulmonary blood flow is calculated on the basis of the change amount of the blood flow signal component (step S16).

Here, the calculated feature amount is at least one of the feature amounts indicating i) speed of pulmonary blood flow, ii) amount of pulmonary blood flow and iii) direction of pulmonary blood flow. In a case where non-overlapping target regions are set, the feature amount is calculated for each target region. In a case where overlapping target regions are set, the feature amount is calculated for each pixel.

i) Speed of Pulmonary Blood Flow

Figure 9A:
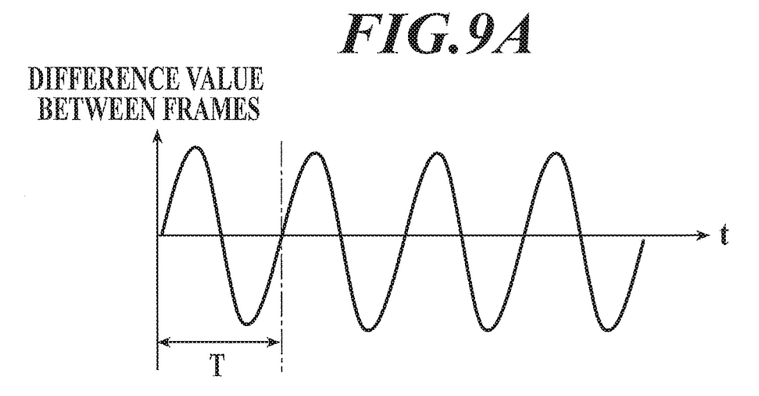
FIG. 9A is a view for explaining an example of feature amount indicating a speed of pulmonary blood flow.
Figure 9B:
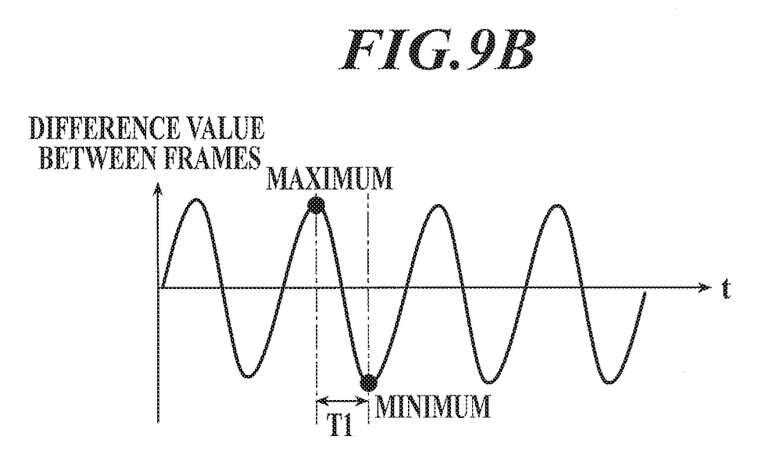
FIG. 9B is a view for explaining another example of feature amount indicating the speed of pulmonary blood flow.

For example, a cycle T[s] is calculated as the feature amount indicating the speed of pulmonary blood flow, the cycle T[s] being a cycle of temporal change regarding the change amount (that is, inter-frame difference value) of blood flow signal component which was calculated in step S15 (see FIG. 9A). Alternatively, a time T1 is calculated as the feature amount indicating the speed of pulmonary blood flow, the time T1 being a time required from a maximum value to the next minimum value in the temporal change of the change amount of the blood flow signal component calculated in step S15 (see FIG. 9B). Alternatively, a differential value is calculated as the feature amount indicating the speed of pulmonary blood flow, the differential value being a differential value of the temporal change of the change amount of the blood flow signal component calculated in step S15. The calculation result is stored in the RAM of control section 31.

ii) Amount of Pulmonary Blood Flow

For example, as the feature amount indicating the amount of pulmonary blood flow, a maximum value or a minimum value in the temporal change of change amount of blood flow signal component calculated in step S15 is calculated. Alternatively, the rate between maximum value and minimum value (maximum value/minimum value) is calculated as the feature amount indicating the amount of pulmonary blood flow. The rate between maximum value and minimum value can show the balance of amount rate between inflow and outflow of blood. The calculation result is stored in the RAM of control section 31.

iii) Direction of Pulmonary Blood Flow

The direction of pulmonary blood flow is obtained if the blood flow in the lung region decreases between frame images and the blood flow increases, in the next frame image, near the position where the blood flow decreased. Here, when the blood flow decreases, the signal value (density value) of dynamic image is changed from low (white) to high (black), and thus, the inter-frame difference value is positive. When the blood flow increases, the signal value (density value) of dynamic image is changed from high (black) to low (white), and thus, the inter-frame difference value is negative. Thus, for each of the target regions (pixels), whether the inter-frame difference value for the t-th frame image is positive or negative is determined. If the inter-frame difference value for a target region (pixel) is positive, the direction of pulmonary blood flow is specified to be the region (pixel) which has the smallest inter-frame difference value among the neighboring regions (for example, eight regions (pixels) around the target region (pixel)) in the "t+1"-th frame image. The information regarding the direction of pulmonary blood flow is stored in the RAM of control section 31.

As described above, in step S16, it is possible to calculate a plurality of indexes indicating pulmonary blood flow functions such as speed, amount and direction of pulmonary blood flow in addition to the change amount of pulmonary blood flow in each of the localized regions of the lung.

Next, the calculation results of the feature amounts of pulmonary blood flow are displayed on the display section 34 (step S17).

Figure 10A:
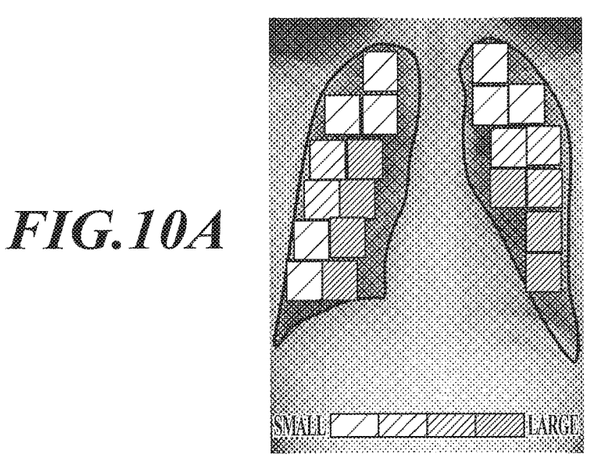
FIG. 10A is a view showing a display example of a calculation result of feature amount regarding a lung in a case where the target regions do not overlap each other.
Figure 10B:
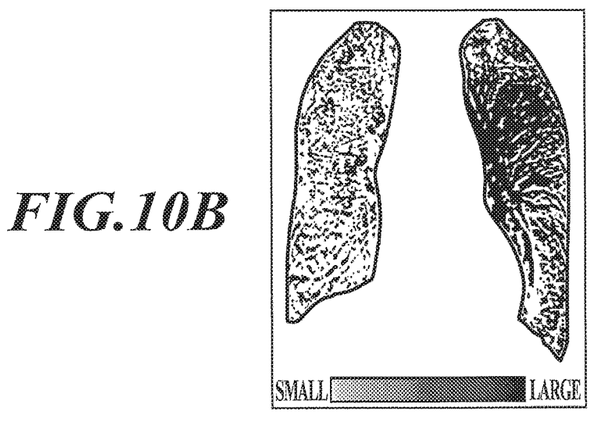
FIG. 10B is a view showing a display example of a calculation result of feature amount regarding a lung in a case where the target regions overlap each other.

For example, in a case where the calculated feature amounts indicate i) speed of pulmonary blood flow or ii) amount of pulmonary blood flow, an image having the target regions (or pixels) in respective colors corresponding to the calculated feature amounts is displayed on the display section 34. FIG. 10A shows an example of result display in a case of non-overlapping target regions. FIG. 10B shows an example of result display in a case of overlapping target regions.

Figure 10C:
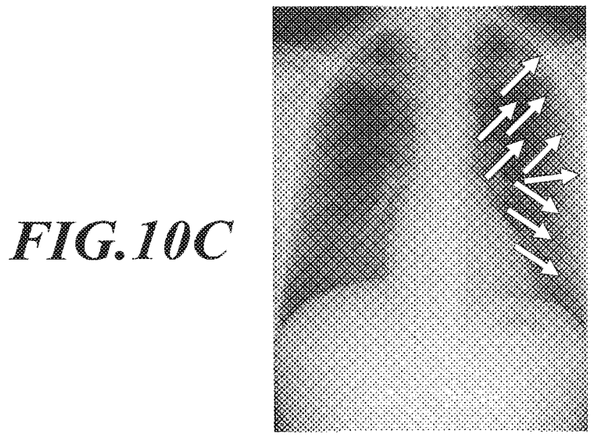
FIG. 10C is a view showing a result display example of a pulmonary blood flow direction.

In a case where the calculated feature amounts indicate the iii) direction of pulmonary blood flow, for example, an image with arrows indicating the directions of blood flow in the lung is displayed on the display section 34. FIG. 10C shows an example of result display of the directions of pulmonary blood flow.

By comparing the pulmonary blood flow function of the central region close to the heart with the pulmonary blood flow function of peripheral regions, it is possible to recognize diseases such as bad blood flow at a peripheral region. That is, by comparing the feature amounts of two regions on the dynamic image, a disease can be found in some cases. Thus, for example, the control section 31 may calculate one of the following (Expression 3) to (Expression 6) to compare the feature amounts of two regions on the image shown in FIG. 10A or FIG. 10B (or reference image), the two regions being specified by a user operating the operation section 33.

rate: $A/B$ (Expression 3)

difference: $|A-B|$ (Expression 4)

cosine similarity: $\cos\theta = A \cdot B / |A||B|$ (Expression 5)

Pearson Correlation:

$$r = \frac{\sum_{i=1}^{n}(A_i - \overline{A})(B_i - \overline{B})}{\sqrt{\sum_{i=1}^{n}(A_i - \overline{A})^2 \sum_{i=1}^{n}(B_i - \overline{B})^2}}$$ (Expression 6)

n: number of compared feature amounts

Here, A is a feature amount of one of the two regions to be compared, and B is a feature amount of the other region to be compared.

In a case where a single feature amount is used for the comparison, the rate or difference is calculated. In a case where a plurality of feature amounts is used for the comparison, the cosine similarity or Pearson correlation is calculated. The calculated value is displayed on the display section 34.

Alternatively, waveforms showing temporal changes of pixel signal values at two regions specified by the operation section 33 may be displayed on the display section 34 so as to be compared with each other.

Figure 11:
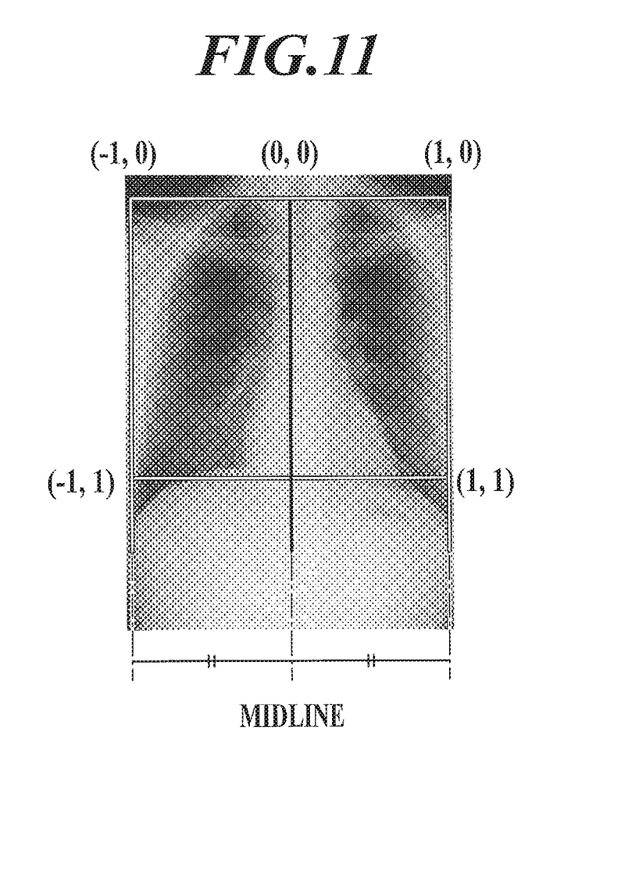
FIG. 11 is a view for explaining normalization of position of lung region when pulmonary blood flow is compared between different dynamic images.

In a case where the pulmonary blood flow function is to be compared between different dynamic images such as lung images of a same subject captured at different times and lung images of different subjects (different patients), the lung position is normalized in order to associate the positions of target regions (pixels) of the lung in the two images with each other. For example, when the comparison is performed between lungs of different dynamic images, a horizontal profile in the x direction is obtained for each of the two dynamic images as shown in FIG. 11, and the position of minimum value of the obtained horizontal profile is determined as the position of midline. Then, the position coordinates of lung region are determined so that the intersection between the midline and the upper end of rectangular region circumscribing the lung region in the frame image is (0, 0), the upper right of rectangular region is (1, 0), the upper left of rectangular region is (-1, 0), the lower right of rectangular region is (1, 1), and the lower left of rectangular region is (-1, 1). The midline may be located at the center of the rectangular region circumscribing the lung region.

As described above, according to the diagnostic console 3, the control section 31 determines a size of target region on the basis of a size of a body part other than the lung blood vessel in the chest dynamic image, a movement amount of a body part other than the lung blood vessel, or subject information attached to the chest dynamic image, the subject information being information regarding the subject of imaging. The control section 31 sets a plurality of target regions having the determined size in the lung region of chest dynamic image. For example, the control section 31 sets the target region size on the basis of the lung size in the chest dynamic image, movement amount of diaphragm, movement amount of rib, or the subject information attached to the chest dynamic image.

Accordingly, it is possible to set an appropriate size of target region in consideration of the influence such as the movement of a body part and the difference between individuals for suppressing noise when analyzing the pulmonary blood flow function in the chest dynamic image.

The control section 31 calculates a representative value of pixel signal values in a set target region, converts the pixel signal values in the target region on the basis of the calculated representative value, extracts the pulmonary blood flow signal from the converted chest dynamic image, and calculates the change amount of the extracted pulmonary blood flow signal. The control section 31 calculates the feature amount regarding pulmonary blood flow on the basis of the calculated change amount of pulmonary blood flow signal.

For example, the control section 31 calculates, as the change amount of pulmonary blood flow signal, the difference value of pixel signal value between frame images generated by extracting the pulmonary blood flow signal from the chest dynamic image, and calculates, as the feature amount regarding the speed of pulmonary blood flow, the cycle of temporal change of the difference value between the frame images, the time required from a maximum point to a minimum point, or a differential value. The control section 31 calculates, as the change amount of pulmonary blood flow signal, the difference value of pixel signal value between frame images generated by extracting the pulmonary blood flow signal from the chest dynamic image, and calculates, as the feature amount regarding the amount of pulmonary blood flow, the maximum value, minimum value or the rate between maximum value and minimum value in the temporal change of difference value between frame images. Further, for example, the control section 31 calculates, as the change amount of pulmonary blood flow signal, the difference value of pixel signal value between frame images generated by extracting the pulmonary blood flow signal from the chest dynamic image, specifies the change direction of pulmonary blood flow signal on the basis of the calculated difference value between frame images, and calculates the specified direction as the feature amount regarding the direction of pulmonary blood flow.

Accordingly, it is possible to provide the information regarding the speed, amount and direction of pulmonary blood flow as diagnosis support information.

The description of the embodiment is an example of a preferred dynamic analysis system according to the present invention, and the present invention is not limited to this embodiment.

For example, the embodiment has been described for an example of using a hard disk or semiconductor non-volatile memory and such like as a computer readable medium of program according to the present invention. However, the present invention is not limited to this example. A portable recording medium such as a CD-ROM can be applied as a computer readable medium. A carrier wave is also applied as the medium for providing program data according to the present invention via a communication line.

As for the other detailed configurations and detailed operations of apparatuses forming the dynamic analysis system 100, modifications can be appropriately made within the scope of the present invention.

The disclosed embodiment is for illustration and not for limitation of the present invention in all respects. The scope of the present invention is indicated by the scope of claims, not by the above description. The scope of the present invention includes the scope of inventions, which is described in the scope of claims, the scope equivalent thereof and all the modifications within the scope of claims.

What is claimed is:

1. A dynamic analysis apparatus, comprising:
a setting section which sets a target region in a lung region of a chest dynamic image which is obtained by radiation imaging;
a conversion section which calculates a representative value of a pixel signal value in the target region set by the setting section, and converts the pixel signal value in the target region on the basis of the calculated representative value;
an extraction section which extracts a pulmonary blood flow signal from the chest dynamic image after conversion by the conversion section; and
a calculation section which calculates a change amount of the pulmonary blood flow signal extracted by the extraction section, and calculates a feature amount regarding pulmonary blood flow on the basis of the calculated change amount of the pulmonary blood flow signal wherein
the extraction section extracts the pulmonary blood flow signal by a method using machine learning.

2. The dynamic analysis apparatus according to claim 1, wherein the extraction section extracts the pulmonary blood flow signal by subtracting a signal waveform of a ventilation component generated by using machine learning from a temporal change waveform showing a temporal change of the pixel signal value in the chest dynamic image after conversion by the conversion section.

3. The dynamic analysis apparatus according to claim 1, wherein the calculation section calculates, as the change amount of the pulmonary blood flow signal, a difference value of the pixel signal value between frame images generated by extracting the pulmonary blood flow signal by the extraction section, and the calculation section calculates, as a feature amount regarding a speed of the pulmonary blood flow, a cycle, a time required from a maximum point to a minimum point or a differential value of a temporal change of the calculated difference value between the frame images.

4. The dynamic analysis apparatus according to claim 1, wherein the calculation section calculates, as the change amount of the pulmonary blood flow signal, a difference value of the pixel signal value between frame images generated by extracting the pulmonary blood flow signal by the extraction section, and the calculation section calculates, as a feature amount regarding an amount of the pulmonary blood flow, a maximum value, a minimum value or a rate between the maximum value and the minimum value of a temporal change of the calculated difference value between the frame images.

5. The dynamic analysis apparatus according to claim 1, wherein the calculation section calculates, as the change amount of the pulmonary blood flow signal, a difference value of the pixel signal value between frame images generated by extracting the pulmonary blood flow signal by the extraction section, identifies a change direction of the pulmonary blood flow signal on the basis of the calculated difference value between the frame images, and calculates the identified direction as a feature amount regarding a direction of the pulmonary blood flow.

6. The dynamic analysis apparatus according to claim 1, further comprising a comparison section which compares the feature amount regarding the pulmonary blood flow calculated by the calculation section or a waveform showing a temporal change of the pulmonary blood flow signal between two or more regions in the lung region.

7. A dynamic analysis system, comprising:
an imaging apparatus which obtains a chest dynamic image by performing radiation imaging of a dynamic state at a chest of a human body; and
the dynamic analysis apparatus according to claim 1.

8. The dynamic analysis system according to claim 7, further comprising a display section which displays an analysis result by the dynamic analysis apparatus.

\* \* \* \* \*